(12) United States Patent
Mills et al.

(10) Patent No.: US 10,780,136 B2
(45) Date of Patent: Sep. 22, 2020

(54) REDUCTION OF MILK GLYCANS AND THEIR DEGRADATION PRODUCTS IN THE NEONATE GUT

(71) Applicant: The Regents of the University of California, Oakland, CA (US)

(72) Inventors: David A. Mills, Davis, CA (US); Steven A. Frese, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/420,032

(22) Filed: May 22, 2019

(65) Prior Publication Data

US 2020/0046783 A1 Feb. 13, 2020

Related U.S. Application Data

(63) Continuation of application No. 15/533,575, filed as application No. PCT/US2015/065323 on Dec. 11, 2015, now Pat. No. 10,350,249.

(60) Provisional application No. 62/091,298, filed on Dec. 12, 2014.

(51) Int. Cl.
*A61K 35/747* (2015.01)
*A01N 63/10* (2020.01)
*C12R 1/225* (2006.01)
*C12N 1/20* (2006.01)

(52) U.S. Cl.
CPC ............ *A61K 35/747* (2013.01); *A01N 63/10* (2020.01); *C12R 1/225* (2013.01); *A61K 2300/00* (2013.01); *C12N 1/20* (2013.01)

(58) Field of Classification Search
None
See application file for complete search history.

(56) References Cited

U.S. PATENT DOCUMENTS

| | | | |
|---|---|---|---|
| 5,849,289 | A | 12/1998 | Dobrogosz et al. |
| 6,797,266 | B2 | 9/2004 | Naidu |
| 2009/0098240 | A1 | 4/2009 | Mills et al. |
| 2013/0244969 | A1 | 9/2013 | Ritter et al. |
| 2014/0120137 | A1 | 5/2014 | Mills et al. |

FOREIGN PATENT DOCUMENTS

| | | |
|---|---|---|
| CN | 103053904 A | 4/2013 |
| WO | 2006/133472 | 12/2006 |
| WO | 2014/153253 A1 | 9/2014 |

OTHER PUBLICATIONS

International Search Report in PCT/US2015/065323, dated Feb. 18, 2016.
Chichlowski et al.; *Annual Review of Food Science and Tech*; vol. 2; 2011; pp. 331-351.
LoCascio et al.; *Agricultural and Food Chem*; vol. 55, No. 22; 2007; p. 8914-8919.
Garrido et al.; *Advances in Nutrition*. vol. 3, No. 3; May 1, 2012; pp. 415S-421S.
Extended European Search Report dated Jul. 23, 2018 for European Patent App. No. 15868025.6.
Afonso Esther Ramalho et al., "Probiotics Association in the Suckling and Nursery in Piglets Challenged with *Salmonella typhimurium*," Brazilian Archives of Biology and Technology, vol. 56, No. 2, Mar. 2013, pp. 249-258.
Casas Ivan A. et al., "Validation of the Probiotic Concept: Lactobacillus Reuteri Confers Broad-Spectrum Protection Against Disease in Humans and Animals," Microbial Ecology in Health and Disease, vol. 12, No. 4, Nov. 2000, pp. 247-285.
Oh Yu-Ri et al., "In Vivo Evaluation of Preventative Effect of Lactobacillus Reuteri on Porcine Epidemic Diarrhea in Suckling Piglets," Korean J Vet Res, vol. 48, No. 2, Jun. 2008, pp. 167-174.
Shim, S. B. et al., "Effects of Feeding Antibiotic-Free Creep Feed Supplemented with Oligofructose, Probiotics or Synbiotics to Suckling Piglets Increases the Preweaning Weight Gain and Composition of Intestinal Microbiota," Archives of Animal Nutrition, vol. 59, No. 6, Dec. 2005, pp. 419-427.
http://www.thepoultrysite.com/articles/1564/probiotics-in-poultry-and-pig-nutrition-basics-and-benefits/Nov. 16, 2009.
Bajagai, Y.S. et al.; http://www.fao.org/3/a-i5933e.pdf; Rome; 2016.
Frese, S.A., et al., "The Evolution of Host Specialization in the Vertebrate Gut Symbiont Lactobacillus Reuteri," PLoS Genetics, 2011, vol. 7, Issue 2, e1001314, www.plosgenetics.org; pp. 1-16.
Frese, S.A., et al., "Comparison of the Colonization Ability of Autochthonous and Allochthonous Strains of Lactobacilli in the Human Gastrointestinal Tract," Scientific Research, Advances in Microbiology, 2012, 2, www.SciRP.org/journal/aim, pp. 399-409.
Frese, S.A., et al., "Molecular Characterization of Host-Specific Biofilm Formation in a Vertebrate Gut Symbiont," PLos Genetics, 2013, vol. 9, Issue 12, e1004057, www.plosgenetics.org; pp. 1-13.
Herfel et al.; *Food and Chemical Toxicology*; vol. 60; Oct. 2013.
Seo et al.; *Asian-Australasian Journal of Animal Science*; vol. 23, No. 12; Dec. 2010; pp. 1657-1667.
Underwood et al.; *Pediatr Res*. Jan. 2015; vol. 77, No. 0; Oct. 2014; pp. 229-235.

*Primary Examiner* — Jennifer E Graser
(74) *Attorney, Agent, or Firm* — Kilpatrick Townsend and Stockton LLP (57) ABSTRACT

Methods of reducing milk glycans, and thus enteric pathogens that use such glycans as carbon sources, in the gut of nursing mammals.

15 Claims, 10 Drawing Sheets

Specification includes a Sequence Listing.

FIG. 10

REDUCTION OF MILK GLYCANS AND THEIR DEGRADATION PRODUCTS IN THE NEONATE GUT

CROSS-REFERENCE TO RELATED PATENT APPLICATIONS

The present application is a continuation of U.S. patent application Ser. No. 15/533,575, filed Jun. 6, 2017, which is a US National Phase of International Application No. PCT/US2015/065323, filed Dec. 11, 2015, which claims the benefit of priority to U.S. Provisional Patent Application No. 62/091,298, filed Dec. 12, 2014, which are incorporated by reference for all purposes.

REFERENCE TO SUBMISSION OF A SEQUENCE LISTING AS A TEXT FILE

The Sequence Listing written in file SequenceListing_1141692.txt created on Oct. 4, 2019, 879 bytes, machine format IBM-PC, MS-Windows operating system, is hereby incorporated by reference in its entirety for all purposes.

BACKGROUND OF THE INVENTION

Sialic acid, released from milk glycans, has been identified as a primary carbon source driving increases in populations of Enterobacteriaceae and Clostridiaceae, which leads to diarrhea in nursing mammals. Data has demonstrated that the bacterial sialidases liberate sialic acid which is consumed by populations of Enterobacteriaceae in the gastrointestinal tract of nursing pigs. This sialic acid is released from milk glycans and host glycans by a bacterial enzyme, sialidase also known as neuraminidase (EC 3.2.1.18). The present technology demonstrates the reduction in sialic acid and N-acetylglucosamine, by delivery of an organism which consumes sialic acid, sialic acid-containing milk glycans, N-acetylglucosamine, or N-acetylglucosamine-containing milk glycans to limit available concentrations of these glycans in vivo. Specifically, this research has shown that this reduction is effective in preventing colonization by these pathogens in nursing animals through this mechanism. Evidence for reduction of Enterobacteriaceae by sialic acid consuming *lactobacillus* is presented.

There are currently no methods which selectively prevent or reduce the growth of Enterobacteriaceae populations in the gut of animals by reducing their nutritional niche in the gut. Piglet diarrhea (scour) and populations of Enterobacteriaceae and Clostridiaceae are controlled at present by antibiotics or vaccines, which do not selectively inhibit the populations of Enterobacteriaceae and prevention strategies.

BRIEF SUMMARY OF THE INVENTION

This disclosure pertains generally to reducing free milk glycans and more specifically to reducing free milk glycan monomers generated by the neonate gut microbiota to eliminate colonization by dysbiotic microbiome members.

From the description herein, it will be appreciated that that the present disclosure encompasses multiple embodiments which include, but are not limited to, the following:

1. A method of altering the composition of the gut bacterial microbiome in nursing non-human mammals to prevent and treat disease, the method comprising: administering to a nursing mammal a dose of an agent that limits the availability of at least one of milk glycans and milk glycan monomers in the nursing mammal's gut; wherein the limited availability of said at least one of milk glycans and milk glycan monomers reduces total populations of enteric pathogens and related organisms in the nursing mammal's gut.

2. The method of embodiment 1, wherein said agent comprises a microbe that competitively utilizes at least one of milk glycans and milk glycan monomers.

3. The method of embodiment 1, wherein said agent comprises a microorganism with the ability to consume a milk glycan monomer.

4. The method of embodiment 1, wherein said agent comprises a bacterium from the genus of at least one of *Lactobacillus* and *Bifidobacterium*.

5. The method of embodiment 4, wherein said agent is administered at dose of $10^4$ to $10^{12}$ colony forming units (CFU).

6. The method of any of embodiments 3-5, further comprising administering at least one prebiotic agent that stimulates colonization of the microorganism in the mammal's gut.

7. The method of embodiment 1, wherein said agent comprises *Bifidobacterium longum* subsp. *infantis*, *B. longum* subsp. *longum*, *B. breve*, or *B. pseudocatenulatum*, or *B. bifidum*.

8. The method of embodiment 1:
wherein said agent comprises a species of bacterium from the genus of at least one of *Lactobacillus* and *Bifidobacterium*;
wherein said species are selected for growth on at least one of milk glycans and milk glycan monomers; and
wherein said growth limits availability of said at least one of milk glycans and milk glycan monomers.

9. The method of embodiment 1, wherein said agent comprises at least $10^{10}$ colony forming units (CFU) of *Lactobacillus reuteri*, selected for growth on gluconate.

10. The method of embodiment 1, wherein said agent is a microorganism possessing any combination of the following characteristics:
genes encoding a neuraminidate lyase (nanA) [sialic acid consumption], sialic acid transporter and/or permease, N-acetylglucosamine transporter or permease, N-acetylglucosamine deacetylase (nagA), glucosamine deaminase (nagB) [nagA and nagB encode for N-acetylglucosamine consumption and sialic acid consumption], fucose transporter and/or permease, fucose isomerase, gluconate transporter and/or permease, gluconate kinase, permeases or transporters capable of transporting complex glycans composed of one or more of the following monomers; sialic acid, fucose, N-acetylglucosamine; or permeases or transporters capable of transporting milk glycans.

11. The method of any of embodiments 1-10, wherein said nursing mammal is a species capable of producing milk containing glycans comprised of at least one of the milk glycan monomers sialic acid, fucose, N-acetylglucosamine, N-acetylgalactosamine, galactose, and glucose.

12. The method of any of embodiments 1-10, wherein said milk glycan monomers are comprised of at least one of the milk glycan monomers selected from the group consisting of sialic acid, fucose, N-acetylglucosamine, N-acetylgalactosamine, galactose, glucose, gluconate, N-acetylmannosamine, N-acetylmannosamine-6-Phosphate, fuculose-1-phosphate, lactaldehyde, and 1,2-propanediol, galactose-1-phosphate, and galactitol.

13. The method of embodiment 4, wherein said agent is administered orally in a live form.

14. The method of embodiment 4, wherein said agent further comprises a prebiotic glycan substrate and wherein said prebiotic glycan substrate is utilized by said bacterium.

15. The method of any of embodiments 1-14, wherein said agent is administered orally in a lyophilized form.

16. The method of any of embodiments 1-15, wherein the mammal is treated with antibiotics.

17. The method of any of embodiments 1-15, wherein the mammal is not treated with antibiotics.

18. The method of any of embodiments 1-17, wherein the mammal is a porcine or bovine mammal.

19. The method of any of embodiments 1-18, wherein the mammal has diarrhea.

20. The method of any of embodiments 1-18, wherein the mammal does not have diarrhea.

21. The method of any of embodiments 1-20, wherein the mammal has an elevated gut concentration of milk glycan monomers or proteobacteria (e.g., Enterobacteriaceae or Bacteroidaceae) prior to the administering 22. The method of embodiment 21, wherein the level of sialic acid in the mammal gut (as measured in the mammal's feces) is at least 1 mg per mg total protein or the level of fucose is at least 1 mg/g feces, or the level of N-acetylglucosamine or N-acetylgalactosamine is at least 10 micrograms/g feces prior to the administering.

23. The method of embodiment 21, wherein (i) at least 10% of the total bacteria community in the mammal's gut is, or (ii) at least $10^7$ cells per gram gut organ contents are Enterobacteriaceae or Bacteroidaceae prior to the administering.

24. The method of embodiment 21, wherein the mammal is tested for the presence of elevated levels of milk glycan monomers or proteobacteria prior or after the administering.

Further aspects of the technology described herein will be brought out in the following portions of the specification, wherein the detailed description is for the purpose of fully disclosing preferred embodiments of the technology without placing limitations thereon.

BRIEF DESCRIPTION OF THE DRAWINGS

The technology described herein will be more fully understood by reference to the following drawings which are for illustrative purposes only.

DETAILED DESCRIPTION OF THE INVENTION

Any nursing non-human mammal (e.g., a porcine or bovine nursing mammal) can be treated with an agent that reduces the availability of at least one milk glycan and/or milk glycan monomer (e.g., sialic acid) in the nursing mammal's gut. The reduction of the milk glycan and/or milk glycan monomer will reduce the total population of enteric pathogens in the mammal's gut by reducing a carbon source of the enteric pathogens.

Exemplary agents that reduce milk glycans and/or milk glycan monomers include but are not limited to microorganisms that consume such glycans, for example, *Lactobacillus* or *Bifidobacterium* bacteria. Bifidobacteria that can be included in the compositions administered to the mammal include, but are not limited to, *B. longum* subsp. *infantis*, *B. longum* subsp. *longum*, *B. breve*, and *B. adolescentis*. The *Bifidobacterium* used will depend in part on the target mammal. *Lactobacillus* that can be included in the compositions administered to the mammal include, but are not limited to, *L. acidophilus*, *L. brevis*, *L. buchneri*, *L. casei*, *L. curvatus*, *L. delbrueckii*, *L. fermentum*, *L. helveticus*, *L. plantarum*, *L. reuteri*, *L. sakei*, or *L. salivarius* or as listed in Table 1 below. In some embodiments, the *Lactobacilli* are from the species *L. delbrueckii*. In some embodiments, the *Lactobacilli* is *Lactobacilli* delbrueckii bulgaris, *Lactobacilli* delbrueckii lactis, *Lactobacilli* delbrueckii delbrueckii, or *Lactobacilli* delbrueckii indicus.

Exemplary bifidobacteria or lactobacilli dosages for formulations can include, but are not limited to, $10^4$ to $10^{12}$ colony forming units (CFU) per dose. A further advantageous range is $10^6$ to $10^{10}$ CFU.

In some embodiments, the mammals are further administered a prebiotic compound that increases colonization by the bifidobacteria or the lactobacilli (i.e., the probiotic). The prebiotic can be administered with the bifidobacteria or the lactobacilli or can be administered within 12 or 24 hours before or after the probiotic is administered. For example, in some embodiments, one or more oligosaccharides that occur in maternal milk can be administered as the prebiotic. Exemplary oligosaccharides are described in, e.g., PCT/US2011/043644. Alternatively, galacto-oligosaccharides (GOS) can be administered as a prebiotic. Optionally, the GOS can be enriched for degree of polymerization that most benefits the probiotic. See, e.g., US2014/0037785.

The probiotic (and optionally prebiotic) can be introduced into the mammal's diet, for example, as an ingredient of animal feed or added to water or milk.

In some embodiments, the enteric pathogenic bacteria population in the mammal's gut prior to administration of the agent includes a population of Enterobacteriaceae (for example, in some embodiments, *E. coli*) or the Bacteroidaceae (for example, in some embodiments, *Bacteroides*). In some embodiments, prior to administration the enteric pathogenic bacteria population (e.g., Enterobacteriaceae (for example, in some embodiments, *E. coli*) or the Bacteroidaceae (for example, in some embodiments, *Bacteroides*)) is at least, e.g., at least 10% of the total bacterial community, more preferably at least 25% or 50% of the total bacterial community, or preferably at least more than $10^7$ cells per gram gut organ contents more preferably at least $10^{10}$ cells per gram gut organ contents. In some embodiments, the enteric pathogenic bacteria population reduced in the mammal's gut includes a reduction in a population of Enterobacteriaceae (for example, in some embodiments, *E. coli*) and the Bacteroidaceae (for example, in some embodiments, *Bacteroides*). In some embodiments, the administration of the agent that reduces the milk glycan or milk glycan monomer results in a reduction of the enteric pathogenic bacteria population (e.g., *E. coli* population) to below, e.g., 50% of the total bacterial community, more preferably less than 10% of the total bacterial community, or preferably less than $10^{10}$ cells per gram gut organ contents more preferably less than $10^7$ cells per gram gut organ contents.

In some embodiments, prior to administration of the agent the level of sialic acid in the mammal gut (as measured in the mammal's feces) is at least 1 mg per mg total protein, or in some embodiments, at least 100 mg/mg total protein, or the level of fucose is at least 1 mg/g feces, or in some embodiments, at least 10 mg/g feces, or the level of N-acetylglucosamine or N-acetylgalactosamine is at least 10 micrograms/g feces or more preferably at least 100 micrograms/g feces. In some embodiments, the administration of the agent that reduces the milk glycan or milk glycan monomer results in a reduction of sialic acid (as measured in the mammal's feces) to less than 100 mg/mg total protein preferably less than 1 mg per mg total protein, or fucose to less than 10 mg/g feces or more preferably less than 1 mg/g feces; or N-acetylglucosamine or N-acetylgalactosamine to less than 100 micrograms/g feces or more preferably less than 10 micrograms/g feces.

Exemplary mammals to which the compositions can be administered include any nursing non-human mammal. Exemplary mammals include, e.g., primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffalos, antelopes, rabbits, and rodents (e.g., guinea pigs, squirrels, rats, mice, gerbils, and hamsters). In some embodiments, the mammal can be under antibiotic treatment (e.g., having received antibiotics within seven, three or one day of receiving the agent that reduces the milk glycan or milk glycan monomer). In other embodiments, the mammal has not received antibiotic treatment or has not received antibiotic treatment in at least one three or seven days prior to receiving the agent that reduces the milk glycan or milk glycan monomer.

In some embodiments, the mammals will be showing signs of enteric pathogen infection or collibacillosis, e.g., diarrhea, within 1, 2, 3, 4, or 5 days prior to treatment with the agent that reduces the milk glycan or milk glycan monomer. Alternatively, the mammal need not have shown a sign of infection by enteric pathogens and is treated prophylactically.

EXAMPLES

Free milk glycan monomers drive pathogen expansion in nursing pigs. Pig scour or collibacillosis is a major cause of illness and death in nursing or weaning pigs worldwide, costing the US alone an estimated $236 million annually through death and disease. Losses resulting from delayed growth are likely to greatly exceed this. The disease itself is characterized by diarrhea that leads to dehydration and death among untreated animals and spreads rapidly within a facility. Costly mitigation procedures must be rapidly implemented and preventative strategies are clearly more economically viable to swine producers. Preventative strategies currently include vaccination, stringent sanitation procedures, and in-feed antibiotics for weaning animals. Despite these preventative strategies, scour remains a major economic cost to swine producers, and a variety of strategies have been explored to control its incidence and spread.

The disease itself is caused by any number of *Escherichia coli* or Clostridia strains able to adhere to the gut epithelium and produce any of a variety of enterotoxins, which leads to tissue damage and diarrhea in the animal. In nursing pigs, particularly, this is a deadly infection and can rapidly lead to severe symptoms or death. While many animals are colonized by benign populations of *E. coli*, enterotoxigenic strains of the species are able to share the same ecological niche. Further, toxigenic strains can only be distinguished from non-toxigenic strains by PCR or ELISA-based assays to identify the presence of toxin encoding genes or the toxins themselves.

Figure 1:
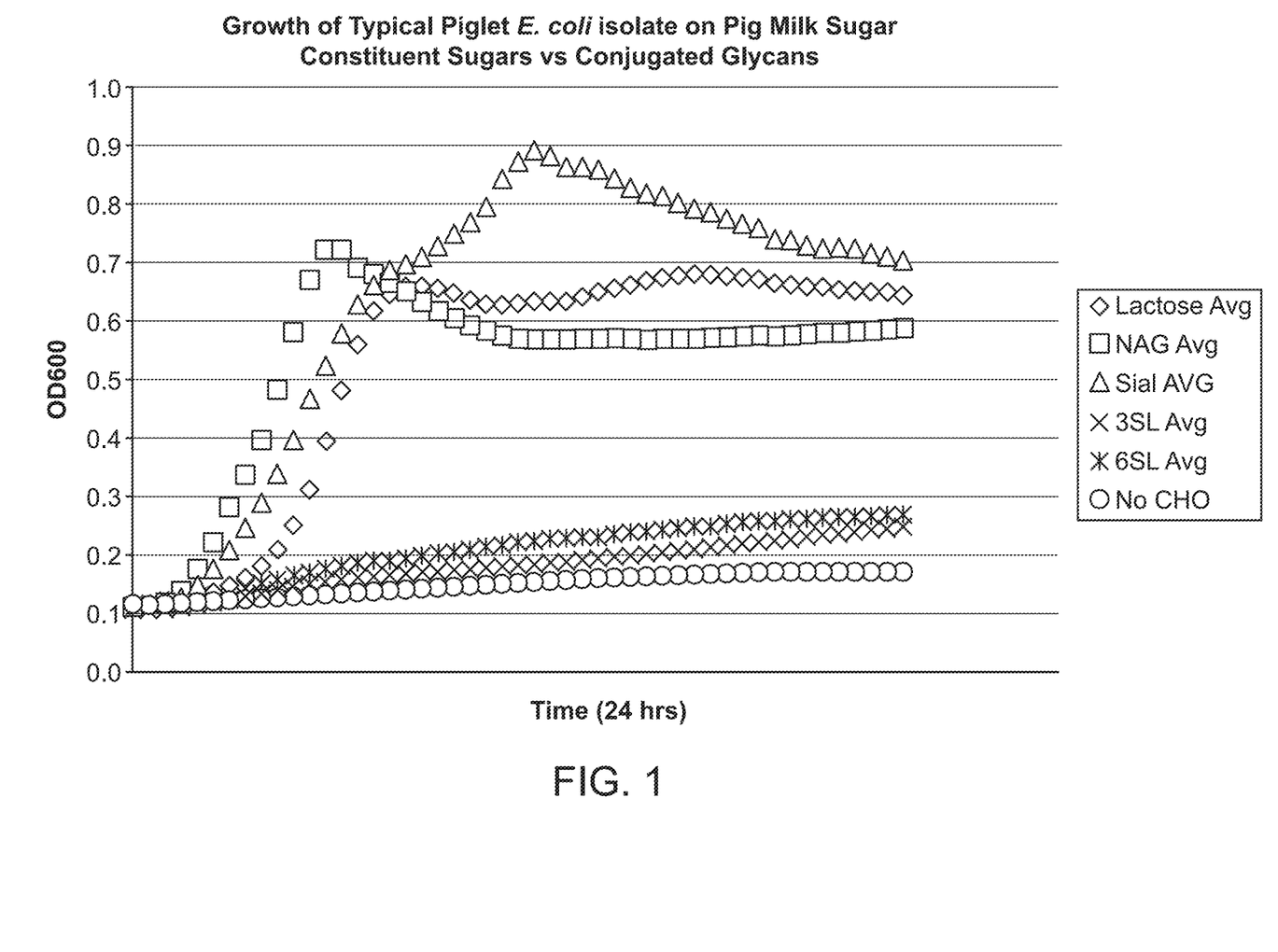
FIG. 1: Graph showing typical piglet *E. coli* isolate on pig milk sugar constituent sugars vs. conjugated glycans.

The nursing pig's diet is primarily composed of milk from the sow. Pig milk contains glycans produced by the lactating sow to nourish nursing pigs and these glycans are composed of monomers of glucose, galactose, N-acetylglucosamine, and sialic acid, with a lesser percentage of fucose monomers (Tao et al 2010). As monomers, these substrates are known to be consumed by *Escherichia* and other organisms that are potentially pathogenic. Other pathogenic organisms may include members of the *Salmonella*, or the Clostridia, which are also associated with gastrointestinal disease in humans and animals, but *E. coli* is the predominant cause of scour in pigs. However, in the form of milk glycans, these complex sugars are indigestible to these organisms. For example, a strain of *Escherichia coli* isolated from the feces of nursing pigs by the inventors is unable to grow on a typical pig milk glycan, sialyllactose, but is able to consume the constituent components (sialic acid, N-acetylglucosamine and lactose) (FIG. 1).

Example Embodiments

Figure 2:
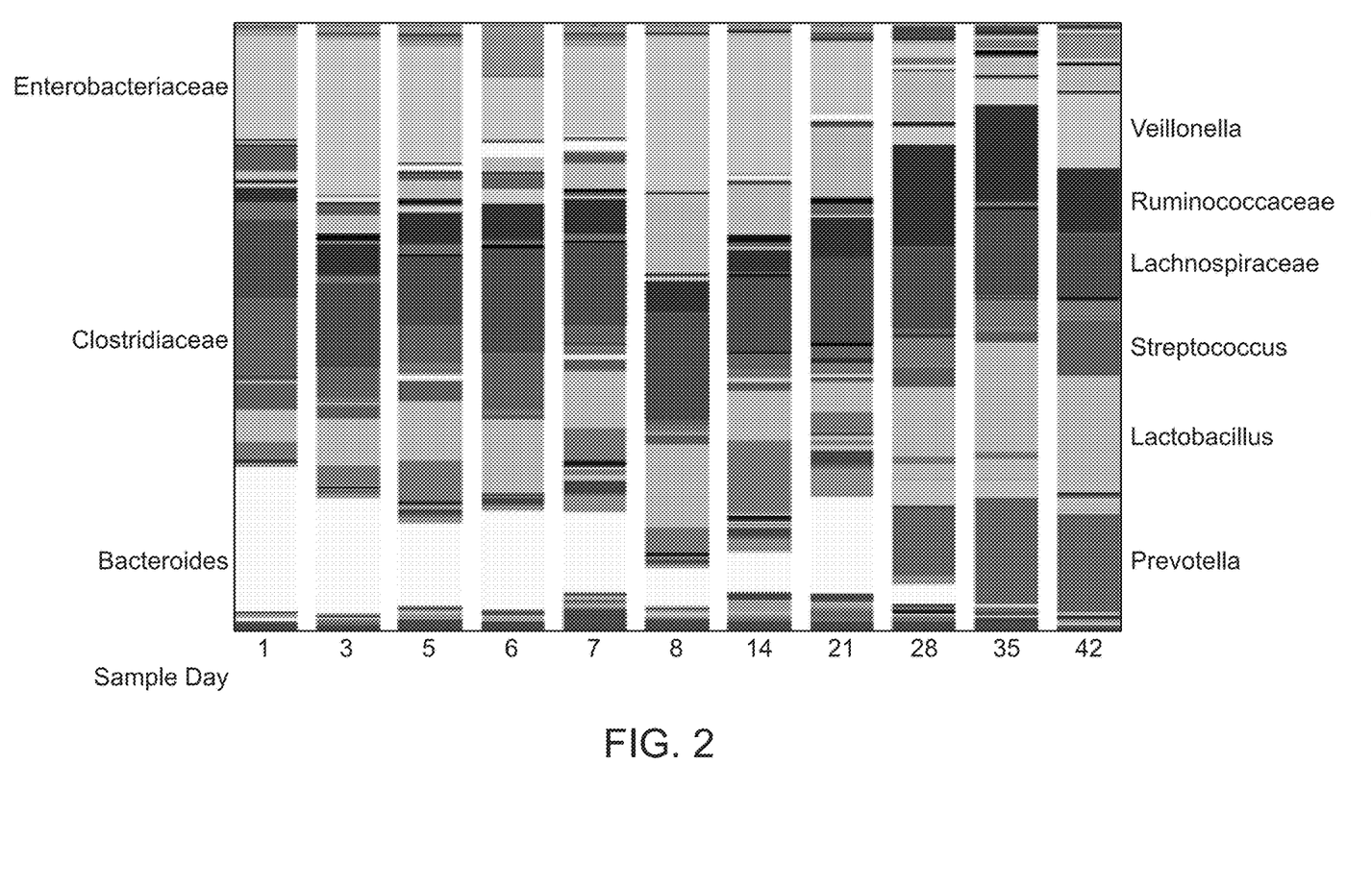
FIG. 2: stacked bar chart showing relative abundance of populations of Bacteroidaceae (in yellow), and in blue, the Enterobacteriaceae are strongly correlated ($r2=0.661$, $p<0.001$) in the feces of young pigs. Communities in weaned animals are boxed.

Data leading to the present technology. To understand the relationship of the gut microbiota with pig milk glycans, the inventors completed an experiment monitoring the temporal changes in the fecal microbiota of pigs from birth through weaning. Fecal microbial populations remained stable while the animals were nursing, but changed dramatically at weaning, when milk glycans were removed from the diet. The dominant taxonomic changes were found during this transition were in the families Enterobacteriaceae (which includes *E. coli*) and the Bacteroidaceae (which includes a genus common to the gut microbiota, *Bacteroides*) (FIG. 2). FIG. 2 shows a stacked bar chart showing relative abundance of populations of Bacteroidaceae (in yellow), and in blue, the Enterobacteriaceae are strongly correlated ($r^2=0.661$, $p<0.001$) in the feces of young pigs. Communities in weaned animals are boxed.

Published *Bacteroides* genomes contain sequences encoding sialidase enzymes, which may separate the sialic acid moiety from sialyllactose, and create an opportunity for *E. coli* to thrive in the gut of the nursing animal, where it may not be able to thrive without the activity of this enzyme. Similarly, the activity of beta hexosaminidases, which remove N-acetylglucosamine monomers from complex glycans also generate a niche for *E. coli* in this manner, as piglet-isolated *E. coli* were found by the inventors to also consume N-acetylglucosamine (FIG. 1). To confirm the presence of these enzymes in the animals, genomic microbial DNA was subjected to metagenomic sequencing, to determine the ecosystem's total metabolic capabilities, and assign taxonomic identities to key metabolic roles. Specifically, we sought to demonstrate that the release of sialic acid and N-acetylglucosamine from pig milk glycans is driven by populations of the gut microbiota.

Figure 3A:
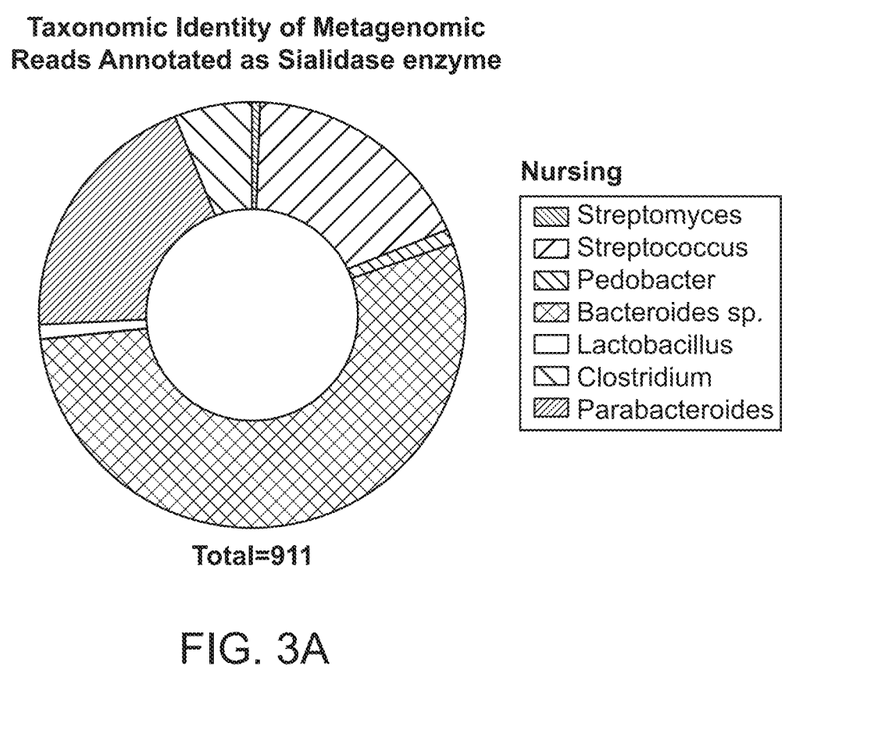
FIG. 3A: Chart showing taxonomic identity of metagenomic reads annotated as sialidase enzyme.
Figure 3B:
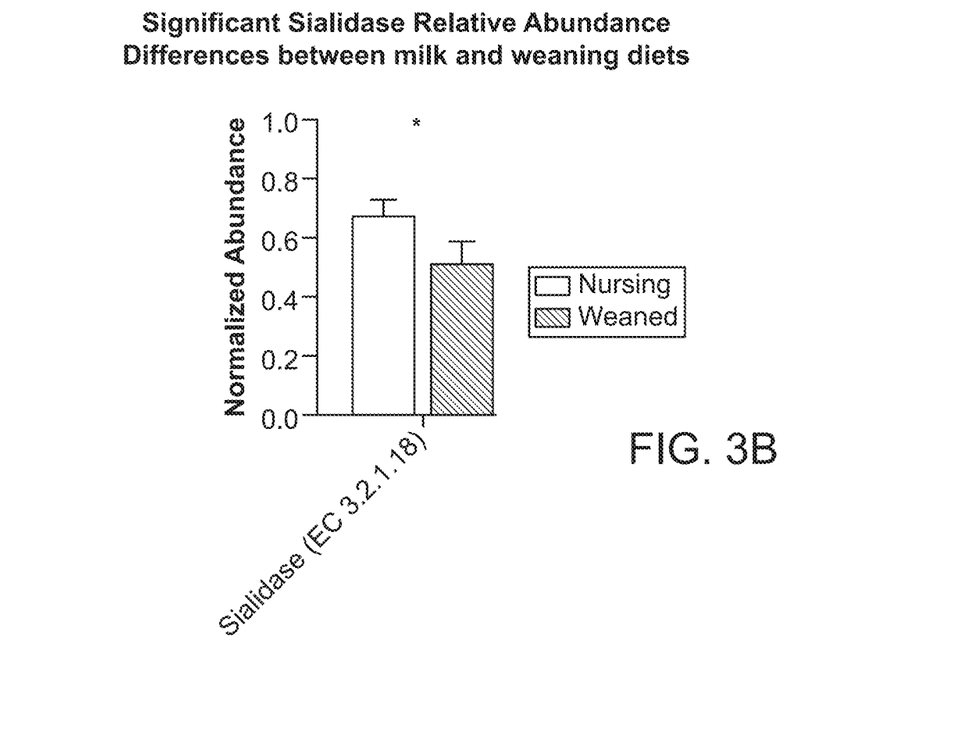
FIG. 3B: Chart showing significant sialidase relative abundance differences between milk and weaning diets.

Genes encoding sialidases and beta hexosaminidases were found to belong to members of the gut microbiota. The taxonomic identity of the bacteria housing these specific enzymes were found to be mostly *Bacteroides* associated with the nursing pigs which diminished when the pigs were weaned (FIG. 3A). Further, the overall abundance of sequencing reads that could be mapped to sialidases declined when the diet of the animals changed to one which contained less of these sugars, suggesting that this enzyme is functionally relevant to populations associated with the pig milk diet but not with the weaned diet composed primarily of oats (FIG. 3B).

Reads that could be classified as a sialidase enzyme and identified taxonomically within the *Bacteroides* were assembled using velvet, to create a full-length hypothetical sialidase sequence. One of the contigs from this assembly was found to contain a full length sialidase-encoding gene belonging to *Bacteroides fragilis*, and matched this gene sequence at 99% nucleotide identity, and was used to generate primers that would amplify this sequence from the total fecal DNA sample.

PCR amplification of the gene, using primers matching the hypothetical sialidase were constructed. These primers successfully amplified a sequence from the total fecal DNA, which was subsequently sequenced at the UC Davis DNA Sequencing core facility. The verified sequence matched the hypothetical sequence generated from metagenomic reads at 100%.

In parallel, a representative *Bacteroides* strain was isolated from fecal samples of nursing pigs by isolation on *Bacteroides* Bile Esculin agar, a selective and discriminative medium for the isolation of *Bacteroides*. Isolated *Bacteroides* strains were found to contain the sialidase by PCR, using the same primers designed previously, and verified by subsequent DNA sequencing at the UC Davis DNA Sequencing Core. The growth of *Bacteroides* on sialyllactose was observed, as this organism clearly possesses a functional sialidase enzyme (data not shown).

Figure 4:
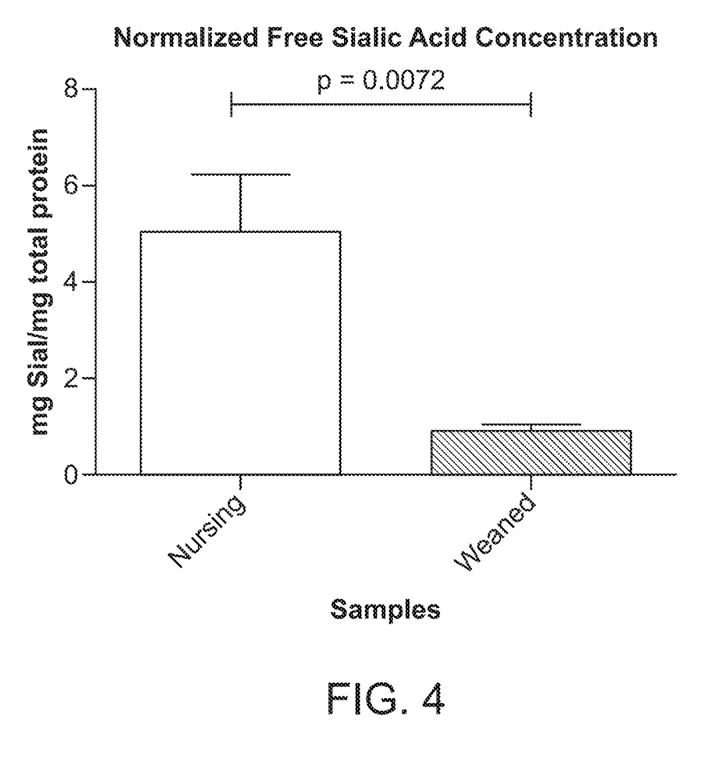
FIG. 4: Chart showing free sialic acid concentration in the feces of nursing and weaned piglets.
Figure 5:
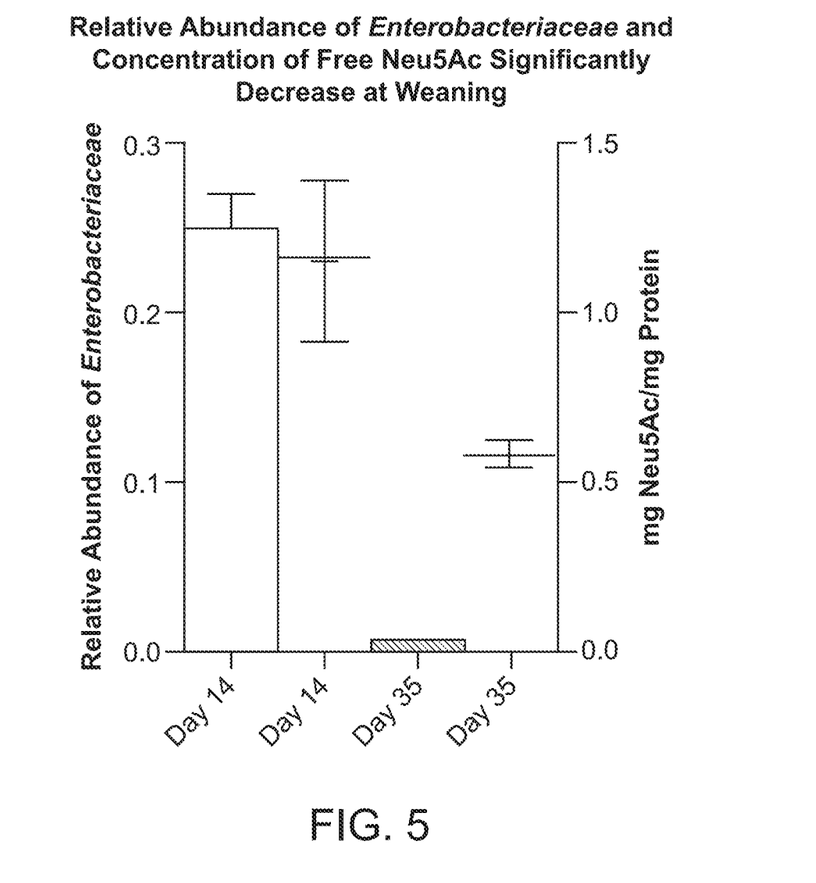
FIG. 5: Chart showing average Enterobacteriaceae populations over time in pigs (left axis, bars, nursing, blue; weaned, red), are significantly different ($p<0.001$) between diets as well as concentrations of free sialic acid, $p<0.001$ (Right axis, whiskers, nursing, blue; weaned, red).
Figure 6:
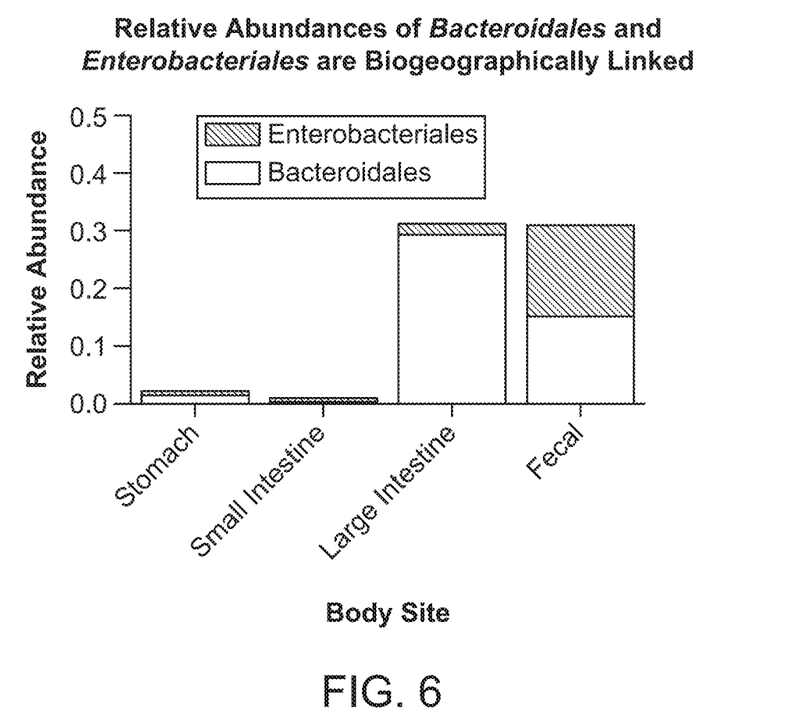
FIG. 6: Chart showing biogeographical relative abundances of Bacteroidales and Enterobacteriaes in the gut of 14 day old nursing pigs.

Further, sialic acid concentrations in these fecal samples could be compared between nursing and weaning diets and was found to be significantly greater in samples with greater *Bacteroides* (and thus sialidase enzyme abundance) abundance (FIG. 4). FIG. 5 shows this data from another perspective. On days where there is a high relative abundance of Enterobacteriaceae, there is a high sialic acid concentration in the feces. On days with low Enterobacteriaceae, there is a low concentration of sialic acid. FIG. 5 shows Average Enterobacteriaceae populations over time in pigs (left axis, bars, nursing, blue; weaned, red), are significantly different ($p<0.001$) between diets as well as concentrations of free sialic acid, $p<0.001$ (Right axis, whiskers, nursing, blue; weaned, red). FIG. 6 shows that this effect appears mostly confined to the caecum and colon of the piglet. There are high *Bacteroides* in the large intestine but and equal bloom of Enterobacteriaceae in the ensuing feces, suggesting that *Bacteroides* is indeed creating a substrate (i.e. sialic acid and more) for Enterobacteriaceae to consume. FIG. 6 shows biogeographical relative abundances of Bacteroidales and Enterobacteriaes in the gut of 14 day old nursing pigs.

Thus, our data can be summarized as (a) that populations of Enterobacteriaceae in the gut of nursing pigs was found to correlate with the abundance of *Bacteroides* ($r2=0.661$, $p<0.001$), (b) and that these populations of Enterobacteriaceae cannot, by themselves, consume sialylated pig milk oligosaccharides, but (c) *Bacteroides* possess enzymes capable of releasing sialic acid from pig milk oligosaccharides, which is (d) associated with increased abundances of sialic acid in feces, which (e) these Enterobacteriaceae can consume.

The synthesis of this knowledge is that monosaccharides released from pig milk glycans leads to increased populations of Enterobacteriaceae in the gut of nursing pigs, creating an environment where the etiological agents of scour can thrive. Specifically, the invention is the knowledge that by reducing the abundance of mono-, di-, or oligomeric sugars, which may include glucose, galactose, N-acetylglucosamine, sialic acid, or fucose derived from milk glycans, will reduce populations of Enterobacteriaceae and other potentially pathogenic organisms capable of consuming these glycans, their breakdown products, or monosaccharides and scour will be prevented or reduced in severity.

This could be accomplished by any approach which reduces concentrations of these monomers or glycans composed of these monomers in the gut. For example, introducing a probiotic microorganism which constitutively and competitively consumes these freed components or glycans could be introduced. As an example, and in no way limiting, Table 1 shows examples of known milk sugar consumers. The species listed have a member (of any subspecies) that possesses genes encoding, for example, a neuraminidate lyase (nanA) [for sialic acid consumption], sialic acid transporter and/or permease, N-acetylglucosamine transporter or permease, N-acetylglucosamine deacetylase (nagA), glucosamine deaminase (nagB) [nagA and nagB encode for N-acetylglucosamine consumption and sialic acid consumption], fucose transporter and/or permease, fucose isomerase, gluconate transporter and/or permease, gluconate kinase, permeases or transporters capable of transporting complex glycans composed of one or more of the following monomers; sialic acid, fucose, N-acetylglucosamine; or permeases or transporters capable of transporting milk glycans.

TABLE 1

Predicted Growth Phenotypes, By Genome Annotations

| Species | Fucose | Sialic Acid | Gluconate | N-acetyl-glucosamine | Lactose |
|---|---|---|---|---|---|
| *Lactobacillus acidophilus* | X | X | | X | X |
| *L. amylovorus* | X | X | X | | X |
| *L. brevis* | X | X | X | X | X |
| *L. buchneri* | X | X | X | X | X |
| *L. casei* | | X | X | X | X |
| *L. crispatus* | X | | | X | X |
| *L. delbrueckii* | | | | X | X |
| *L. fermentum* | X | | X | | X |
| *L. gasseri* | | | | X | X |
| *L. helveticus* | X | X | | X | X |
| *L. johnsonii* | X | X | | X | X |
| *L. kefiranofaciens* | X | | | X | X |
| *L. paracasei* | | | X | | X |
| *L. plantarum* | X | X | X | X | X |
| *L. reuteri* | X | | X | X | X |
| *L. rhamnosus* | X | | X | X | X |
| *L. ruminus* | X | | | X | X |
| *L. sakei* | X | X | X | X | X |

TABLE 1-continued

Predicted Growth Phenotypes, By Genome Annotations

| Species | Fucose | Sialic Acid | Gluconate | N-acetyl-glucosamine | Lactose |
|---|---|---|---|---|---|
| L. salivarius | X | X | | X | X |
| B. adolescentis | X | X | X | X | X |
| B. animalis | X | X | X | X | X |
| B. asteroides | X | | X | | X |
| B. bifidum | X | X | X | X | X |
| B. breve | X | X | X | X | X |
| B. dentium | X | | X | X | X |
| B. longum | X | X | X | X | X |
| B. thermophilum | X | X | | | X |

Figure 7:
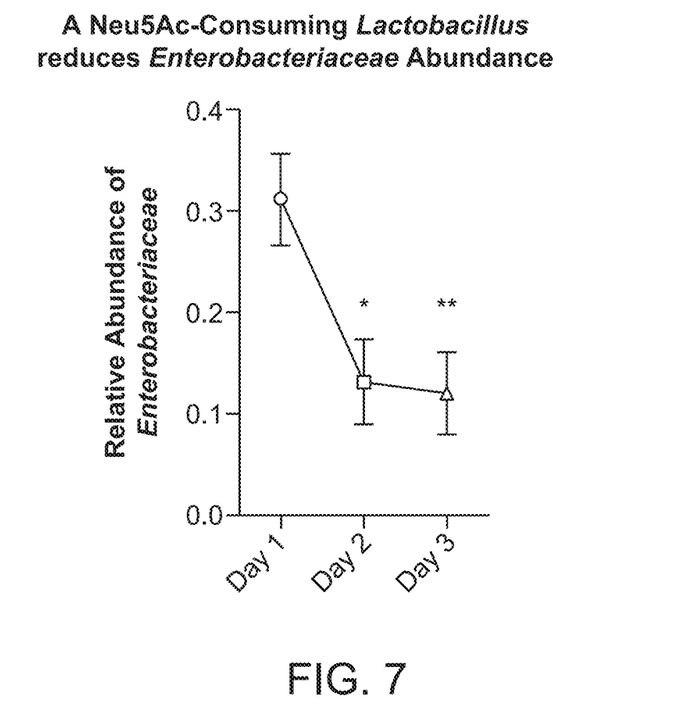
FIG. 7: Graph showing treating 14 d old pigs by gavage with *Lactobacillus* UCD14261 led to significant reductions in Enterobacteriaceae populations.

To test this we isolated a *Lactobacillus reuteri* strain from pig feces that is able to grow on gluconate. This strain was grown to high cell densities and $10^{10}$ CFU was used to gavage 14 d old piglets daily for three days in a pilot experiment. Fecal samples were collected prior to gavage and two days thereafter, and these were analyzed by 16S rRNA amplicon sequencing. Importantly we found that relative populations of Enterobacteriaceae decreased significantly, compared to baseline samples (FIG. 7), despite these populations remaining otherwise stable during nursing in previous studies in age-matched pigs (FIG. 2). Thus, our preliminary data provides tantalizing evidence that our hypothesized mechanism (and solution) may be effective in reducing Proteobacteria populations. Specifically, FIG. 7 shows the treating 14 d old pigs by gavage with *Lactobacillus* UCD14261 led to significant reductions in Enterobacteriaceae populations.

Figure 8:
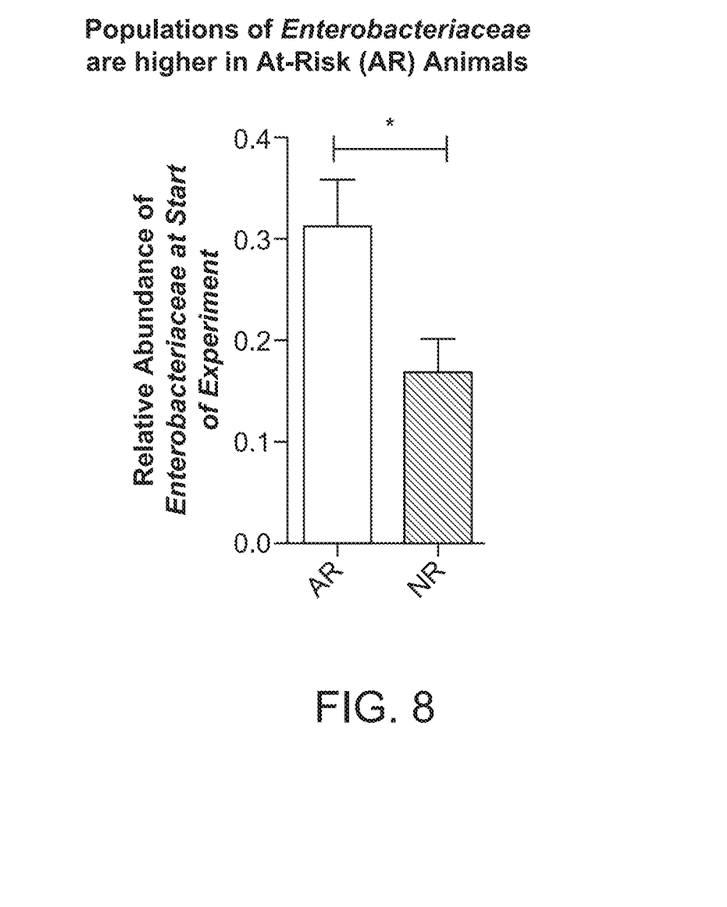
FIG. 8: Chart showing distinct differences in "At risk" or high-Enterobacteriaceae versus "NR" "No risk" pigs prior to gavage with *Lactobacillus*.
Figure 9:
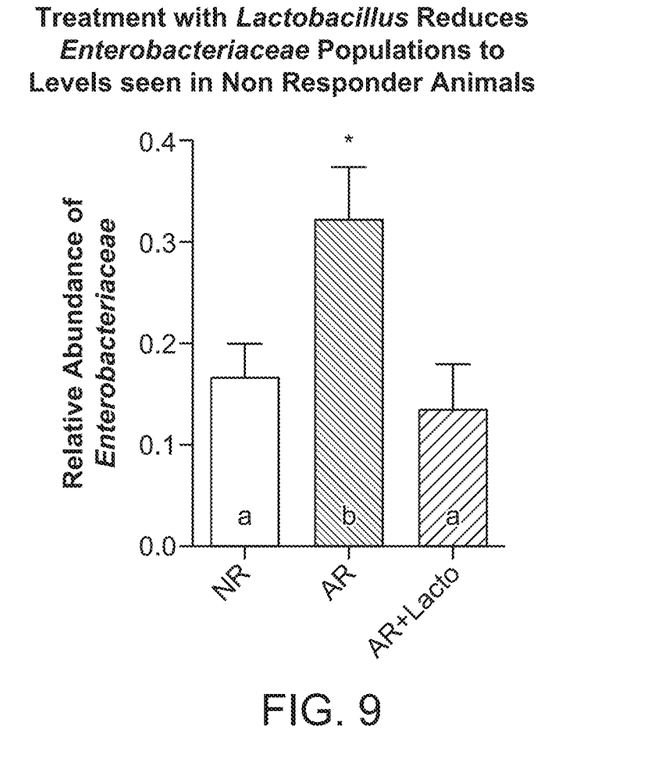
FIG. 9: Chart showing "at risk" (AR) or high-Enterobacteriaceae pigs could be rescued by gavage with *Lactobacillus* to resemble No Risk or Non Responder animals. Letters denote significance groups (a, b; $p<0.05$).

We also identified a distinction between populations of piglets even within the same litter. Some animals (7/11) harbored higher ($p<0.05$) populations of Enterobacteriaceae, which were, on average twice the average population found in low-Enterobacteriaceae animals (4/11 animals) (FIG. 8). FIG. 8 gives distinct differences in "At risk" or high-Enterobacteriaceae versus "NR" "No risk" pigs prior to gavage with *Lactobacillus*. These piglets responded differently to supplemented *Lactobacillus reuteri* UCD14261, where animals harboring high Enterobacteriaceae populations (which we termed "At-Risk" (AR) animals) showed significant drops in these organisms after gavage with *Lactobacillus* (FIG. 9), populations in the low-Enterobacteriaceae animals were largely unaffected. These "at risk" animals had significantly lower populations of starting Lactobacillaceae populations ($p<0.05$), which may help explain why higher populations of Enterobacteriaceae could thrive, and why supplementation with *Lactobacillus* led to a reduction where populations of Enterobacteriaceae were not significantly different from low-Enterobacteriaceae animals. FIG. 9 shows "At risk" (AR) or high-Enterobacteriaceae pigs could be rescued by gavage with *Lactobacillus* to resemble No Risk or Non Responder animals. Letters denote significance groups (a, b; $p<0.05$).

Figure 10:
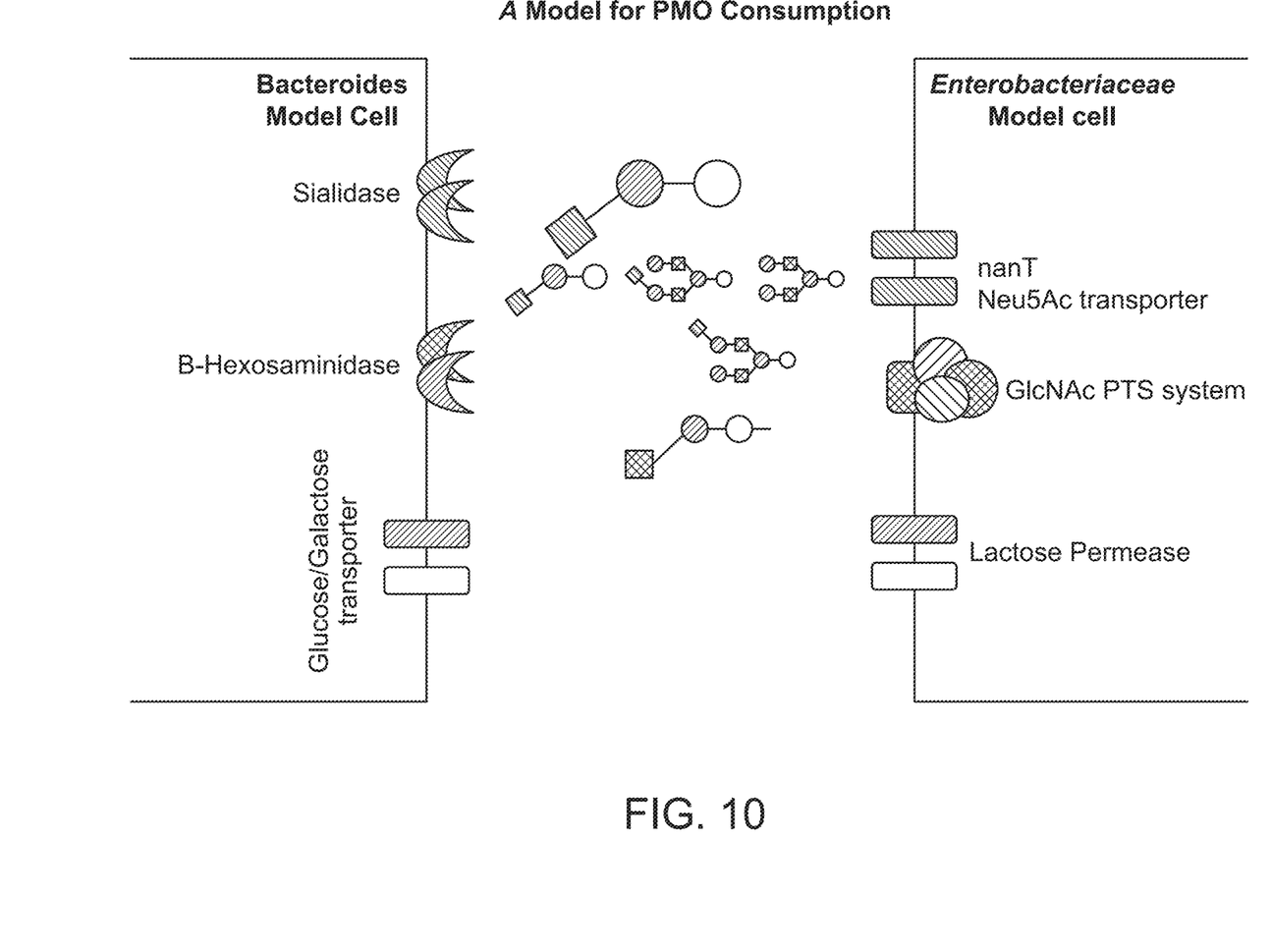
FIG. 10: Model for PMO Consumption.

FIG. 10 shows a model for PMO consumption.

Materials and Methods

All experiments involving animals were reviewed and approved by the University of California Davis Institutional Animal Care and Use Committee prior to experimentation (Approval #17776, #18279). Throughout the study, all animals were housed in a controlled-access specific pathogen free facility at the University of California Davis dedicated to the rearing of pigs. Three healthy adult pregnant sows from the University of California herd were selected for this study. Upon delivery, the infant pigs were cohoused with sows and ear tagged for identification, following standard practices. The piglets were allowed to nurse freely until weaning after 21 days of age. Piglets were removed from the sow and transferred to separate housing and fed a standard starter feed (Hubbard Feeds Mankato, Minn. USA) after 21 days of age. Animals were given ad libitum access to water and feed. Milk was collected from sows while nursing their respective litters and stored at −80 C.

Sampling. Fecal samples were collected using a sterile cotton swab (Puritan Medical, Guilford, Me. USA) rectally from each piglet after 1, 3, 5, 7, 14, 21, 28, 35, and 42 days after birth. Swabs were also used to collect fecal samples from mother sows and ~4 $cm^2$ sites within the enclosure throughout the study.

Sequencing Library Construction. DNA was extracted from swabs using the Zymo Research Fecal DNA kit (Zymo Research Irvine, Calif. USA) according to the manufacturer's instructions. Extracted DNA was used as a template for PCR using barcoded primers to amplify the V4 region of the 16S rRNA gene as previously described for bacteria and the internal transcribed spacer region (ITS) to assess fungal communities {Bokulich:2013uf, Bokulich:2013vd}.

Briefly, the V4 domain of the 16S rRNA gene was amplified using primers F515 (5'-NNNNNINNNGTGTGC-CAGCMGCCGCGGTAA-3'; SEQ ID NO:1) and R806 (5 L GGACTACHVGGGTWTCTAAT-3'; SEQ ID NO:2), where the poly-N (italicized) sequence was an 8-nt barcode unique to each sample and a 2-nt linker sequence (bold). PCR amplification was carried out in a 15 μL reaction containing 1×GoTaq Green Mastermix (Promega, Madison, Wis. USA), 1 mM $MgCl_2$, and 2 pmol of each primer. The amplification conditions included an initial denaturation step of 2 minutes at 94° C., followed by 25 cycles of 94° C. for 45 seconds, 50° C. for 60 seconds, and 72° C. for 90 seconds, followed by a single final extension step at 72° C. for 10 minutes. All primers used in this study are summarized in Table S1. Amplicons were pooled and purified using a Qiagen PCR purification column (Qiagen) and submitted to the UC Davis Genome Center DNA Technologies Sequencing Core for paired-end library preparation, cluster generation and 250 bp paired-end sequencing on an Illumina MiSeq. Fungal and bacterial amplicons were sequenced in separate MiSeq runs Quality-filtered demultiplexed reads were analyzed using QIIME 1.8.0 {Kuczynski:2012gz, Walters:2010ts} as previously described {Bokulich:2014tx}, except the 13_8 greengenes database release was used for OTU picking and taxonomy assignment and bacterial sequences were aligned using UCLUST {Edgar:2010cv}. 7 000 sequences per sample were randomly subsampled for analysis of bacterial communities to ensure suitable comparisons. Samples with fewer than 7 000 sequences were omitted. Alpha diversity estimates were computed for phylogenetic diversity (PD) whole tree and compared by nonparametric two-sample t-test with Bonferroni correction and 999 Monte Carlo permutations for bacterial analyses. Beta diversity was calculated by weighted (or unweighted, where noted) UNIFRAC metrics for bacterial populations {Lozupone:2005gn}.

Metagenome sequencing. Total genomic DNA was extracted from fecal samples with the ZYMO Research Fecal DNA Extraction kit according to manufacturer instructions and prepared using the Illumina MiSeq v3 Reagent Chemistry for whole genome shotgun sequencing of multiplexed 150 bp libraries at the University of California Davis Genome Sequencing Core (http://dnatech.genomecenter.ucdavis.edu). Samples were pooled and sequenced across triplicate sequencing runs. FASTQ files were demultiplexed, quality filtered, trimmed to 150 bp, and then reads for each sample were pooled from the three runs, yielding 15-20 million reads per sample, and submitted to the MGRAST pipeline for analysis {Glass:2010ke}, which removes host genomic DNA reads and duplicate reads, bins 16S rRNA reads, and functionally classifies remaining reads by predicted protein sequence. Classified reads were normalized in MGRAST and compared between treatments using STAMP {Parks:2014hi}.

Isolation of PMG-Consuming *Bacteroides* and *Escherichia coli*. Fecal samples were diluted in phosphate buffered saline (pH 7.0) and plated onto pre-reduced *Bacteroides* Bile Esculin Agar (HiMedia Mumbai, India) plates and incubated at 37° C. anaerobically for 2 d, then subcultured to purity and typed using a MALDI-TOF Biotyper (Bruker Corporation Fremont Calif., USA) according to manufacturer's instructions. 16S rRNA sequencing using primers 8F and 1391R were used to confirm identity. *Bacteroides* were cultured in BHI-S overnight, anerobically at 37° C. *Bacteroides* was grown in minimal medium for growth assays, as described previously {Martens:2008kp}, using lactose, glucose, galactose, 2,3-sialyllactose, 2,6-sialyllactose, sialic acid as sole carbon sources (1% w/v).

Identification of sialic-acid consuming *Lactobacillus* species. Fecal samples from nursing and weaned pigs were cultured on Rogosa SL media containing glucose, raffinose, or ribose as sole carbon sources and grown at 37 or 45 C anaerobically, to preferentially isolate species of *Lactobacillus*. Colonies were isolated to purity and initially identified using a MALDI-TOF Mass Spectrometer and BioTyper system (Bruker, Fremont, Calif. USA). Genomic DNA was extracted as described previously {Oh:2009bo} and partial 16S rRNA sequences were generated by PCR using primers 8F and 581R under cycling and reaction conditions described elsewhere {Bokulich:2013vd}. Isolates were grouped at the species level and representatives selected for growth screening and 16S rRNA determination. Sequences were determined by the UC Davis DNA Sequencing Core (http://dnaseq.ucdavsis.edu) and compared to the NCBI 16S rRNA database to confirm MALDI-BioTyper identification. Representative isolates were screened for the ability to grow on (1% w/v) sialic acid or N-acetylglucosamine as sole carbon sources in basal MRS medium containing these as a sole carbon source. Lactose and glucose were also compared as positive controls. *Lactobacillus* genomes available in the JGI-IMG database were screened for the presence of a complete sialic acid utilization repertoire.

Genome Sequencing. *Lactobacilli*, *Bacteroides* spp. isolated from nursing piglet fecal samples and possessing the sialidase predicted by metagenomic sequencing, and the *Escherichia coli* containing the sialic acid catabolism pathway as determined by PCR, were selected for whole genome shotgun sequencing on an Illumina HiSeq at the UC Berkeley Vincent J. Coates Genomics Sequencing Laboratory (http://qb3.berkeley.edu/qb3/gsl/index.cfm). Reads were assembled using velvet {Zerbino:2008vu}, yielding an average coverage >20-fold, and uploaded to the JGI database for annotation and public deposition.

Detection of sialic acid in feces. Fecal samples were suspended in 500 uL of dH2O and vortexted for 30 m at 2500RPM and then centrifuged at 14 000 RPM for 15 minutes, from which the supernatant was removed. Two additional extractions of the pellet were performed for a final volume of 1.5 mL. 150 uL was removed for protein quantification using the Bradford Assay, with BSA to generate a standard curve. Samples were purified on an anion-exchange resin and eluted with 5 mL 50 mM NaCl and dried under vacuum before reconstituting in 500 uL dH2O. Sialic acid concentrations were determined using a commercial kit according to the manufacturer's instructions (Abcam Cambridge, Mass. USA). The sialic acid concentration is normalized to total protein concentration and expressed as mg sialic acid per mg protein.

Statistical Analysis. T-tests and linear correlations were calculated using Graph Pad Prism 6 for OSX (Graph Pad Software, La Jolla, Calif. USA) with a minimum p value of 0.05.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

In addition to any other claims, the applicant(s)/inventor(s) claim each and every embodiment of the technology described herein, as well as any aspect, component, or element of any embodiment described herein, and any combination of aspects, components or elements of any embodiment described herein.

All cited references are incorporated herein by reference in their entirety.

What is claimed is:

1. A method of preventing or reducing severity of scour in a pig, the method comprising administrating a therapeutically-effective dose of *Bifidobacterium longum* subsp. *infantis* to the pig.

2. The method of claim 1, wherein said agent is administered at dose of $10^4$ to $10^{12}$ colony forming units (CFU).

3. The method of claim 1, further comprising administering at least one prebiotic agent that stimulates colonization of *Bifidobacterium longum* subsp. *infantis* in the pig's gut.

4. The method of claim 1, wherein said *Bifidobacterium longum* subsp. *infantis* is administered orally.

5. The method of claim 1, wherein said *Bifidobacterium longum* subsp. *infantis* further comprises a prebiotic glycan substrate and wherein said prebiotic glycan substrate is utilized by said *Bifidobacterium longum* subsp. *infantis*.

6. The method of claim 1, wherein said *Bifidobacterium longum* subsp. *infantis* is administered orally in a lyophilized form.

7. The method of claim 1, wherein the pig is treated with antibiotics.

8. The method of claim 1, wherein the pig is not treated with antibiotics.

9. The method of claim 1, wherein the pig has diarrhea.

10. The method of claim 1, wherein the pig does not have diarrhea.

11. The method of claim 1, wherein the pig has an elevated gut concentration of milk glycan monomers or proteobacteria prior to the administering.

12. The method of claim 11, wherein the level of sialic acid in the pig's gut as measured in the pig's feces is at least 1 mg per mg total protein or the level of fucose is at least 1 mg/g feces, or the level of N-acetylglucosamine or N-acetylgalactosamine is at least 10 micrograms/g feces prior to the administering.

13. The method of claim 11, wherein (i) at least 10% of the total bacteria community in the pig's gut is Enterobacteriaceae or Bacteroidaceae prior to the administering, or (ii) at least $10^{10}$ cells per gram gut organ contents are Enterobacteriaceae or Bacteroidaceae prior to the administering.

14. The method of claim 1, wherein the pig is tested for the presence of elevated levels of milk glycan monomers or proteobacteria prior or after the administering.

15. The method of claim 1, wherein the pig is a nursing piglet.

* * * * *

SEQUENCE LISTING

```
<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: synthetic primer F515
<220> FEATURE:
<221> NAME/KEY: misc_feature
```

```
<222> LOCATION: (1)..(29)
<223> OTHER INFORMATION: n is a, t, c or g

<400> SEQUENCE: 1
nnnnnnnngt gtgccagcmg ccgcggtaa                                    29

<210> SEQ ID NO 2
<211> LENGTH: 20
<212> TYPE: DNA
<213> ORGANISM: Artificial Sequence
<220> FEATURE:
<223> OTHER INFORMATION: synthetic primer R806

<400> SEQUENCE: 2
ggactachvg ggtwtctaat                                              20
```